(12) United States Patent
Joshi et al.

(10) Patent No.: US 6,359,003 B1
(45) Date of Patent: Mar. 19, 2002

(54) USE OF FUMARIC ACID DERIVATIVES IN TRANSPLANT MEDICINE

(75) Inventors: Rajendra Kumar Joshi, Zürich; Hans-Peter Strebel, Muri, both of (CH)

(73) Assignee: Fumapharm AG, Muri (CH)

( * ) Notice: Subject to any disclaimer, the term of this patent is extended or adjusted under 35 U.S.C. 154(b) by 0 days.

(21) Appl. No.: 09/719,189

(22) PCT Filed: Aug. 20, 1999

(86) PCT No.: PCT/EP99/06110

§ 371 Date: Dec. 8, 2000

§ 102(e) Date: Dec. 8, 2000

(87) PCT Pub. No.: WO00/12072

PCT Pub. Date: Mar. 9, 2000

(30) Foreign Application Priority Data

Aug. 31, 1998 (DE) .......................... 198 39 566

(51) Int. Cl.⁷ ....................... A61K 31/225; A61K 31/19
(52) U.S. Cl. ........................... 514/547; 514/557
(58) Field of Search ................. 514/547, 557

(56) References Cited

U.S. PATENT DOCUMENTS

| | | | |
|---|---|---|---|
| 4,851,439 A | * 7/1989 | Speiser et al. | 514/547 |
| 4,959,389 A | * 9/1990 | Speiser et al. | 514/547 |
| 5,149,695 A | * 9/1992 | Speiser et al. | 514/75 |
| 5,424,332 A | * 6/1995 | Speiser et al. | 514/547 |
| 5,451,667 A | * 9/1995 | Speiser et al. | 536/41 |
| 6,277,882 B1 | * 8/2001 | Joshi et al. | 514/547 |

FOREIGN PATENT DOCUMENTS

| | | |
|---|---|---|
| WO | 9627369 | 9/1996 |
| WO | 9804290 | 2/1998 |
| WO | 9827970 | 7/1998 |
| WO | 9852549 | 11/1998 |

OTHER PUBLICATIONS

Nathens, et al., "The Glutathione Depleting Agent Diethylmaleate Prolongs Renal Allograft Survival", Journal of Surgical Research, vol. 77, 1998, pp. 75–79.

Schwinghammer et al., "Pharmacologic prophylaxis of acute graft–versus–host disease after allogeneic marrow transplantation", Therapy, Reviews Clinical Pharmacy, vol. 12, Oct. 1993, pp. 736–761.

Gasser, et al., "Host Vs Graft and Graft Vs Host Reactions After Allogeneic Heterotopic Small Bowel Transplantation in the Rat", Transplantation Proceedings, vol. 24, No. 3, Jun. 1992, pp. 1128–1129.

* cited by examiner

*Primary Examiner*—Kevin E. Weddington
(74) *Attorney, Agent, or Firm*—Sieberth & Patty, L.L.C.

(57) ABSTRACT

The invention relates to the use of certain fumaric acid monoalkyl esters as salts or a free acid either alone or in combination with a dialkyl fumarate for producing pharmaceutical preparations for use in transplantation medicine, especially for treating, alleviating or suppressing host-versus-graft reactions. For this purpose, the fumaric acid monoalkyl esters may be used in combination with preparations conventionally used in transplantation medicine and immuno suppressives, especially such as cyclosporines.

18 Claims, No Drawings

USE OF FUMARIC ACID DERIVATIVES IN TRANSPLANT MEDICINE

This application is a 371 continuation of PCT Application PCT /EP99/066110, fiked Aug. 20, 1999, the text of which is not English, which PCT Application claims priority on German Application No. 198 39 566.3, filed Aug. 31, 1998, the text of which is not in English.

The present invention relates to the use of certain fumaric acid monoalkyl esters either in the form of salts thereof or as the free acid, alone or in combination with a dialkyl fumarate, for preparing pharmaceutical compositions for use in transplantation medicine. In particular, it relates to the use of said pharmaceutical preparations containing fumaric acid alkyl esters for treating, alleviating or suppressing rejection of the transplant by the recipient, i.e. host-versus-graft reaction.

Transplantations are tissue or organ transplantations, i.e. the transfer of tissue such as cornea, skin, bones (bone chips), vessels or fasciae, of organs such as kidney, heart, liver, lung, pancreas or intestine, or of individual cells such as islet cells, $\alpha$-cells and liver cells, the kidney having the greatest significance as a transplanted organ.

According to the degree of relationship between the donor and the recipient we differentiate between auto-transplantation (transfer to another part of the body of the same individual), iso-transplantation (transfer to another, genetically identical individual) or allogenic transplantation (transfer to another individual of the same species). Depending on the site of origin and transplantation, we further differentiate between homotopic transplantation (transfer to the same site) and heterotopic transplantation (transfer to a different site). The above-mentioned transplantations play an important role in modern medicine.

A major problem in transplantation medicine is graft rejection after transplantation of the tissue, organ or cell by immunological defence reactions of the recipient. Such a graft rejection is also called host-versus-graft reaction. The immunological defence reaction of the organism against the heteroprotein often results in rejection or dissolution of the grafts. By using modern immunosuppressive agents, the most important representatives of which are the cyclosporines, especially cyclosporine A, a significant improvement in the results of transplantations was achieved over the last few years. At present, the one-year survival rate is about 60% for liver transplantations, about 80% for heart transplantations and over 90% for kidney transplantations.

In host-versus-graft reactions, different stages may be distinguished. Depending on the degree of difference between the recipient and the donor, this reaction takes place at different speeds so that we speak of a an acute, sub-acute or chronic reaction. Acute rejection processes are accompanied by the irreversible loss of the transplant (necrotisation) as a result of arteriitis or arteriolitis within 48 hours and cannot be influenced by the administration of drugs. The subacute rejection reaction becomes manifest as a rejection crisis from day 12 to month 4 with reversible functional disorders as a result of a transplant vasculopathy. Finally, the loss of function of the transplant as a result of vascular changes such as obliterating arteriopathy, which proceeds over weeks or years and can practically not be influenced by drugs, is termed a chronic rejection reaction.

To avoid such rejection reactions, i.e. the host-versus-graft reaction, transplantation medicine essentially makes use of immunosuppression, i.e. a weakening of the normal immunoresponse. For this purpose, anti-lymphocyte sera are often used in combination with corticosteroids and so-called anti-metabolites, e.g. purine analogues such as 6-mercaptopurine and thioguanine which affect the nucleic acid and protein synthesis and thus prevent cell division and proliferation. This leads to suppression of the production of antibodies and the cellular immune response. The immunosuppressive agents used for therapy are substances which suppress or weaken the immunoreaction in the body either specifically or non-specifically. Non-specific immunosuppressive agents are cytostatic agents such as, for example, alkylating agents or antimetabolites. In addition, active ingredients are known which cause at least partial specific immunosuppression, such as corticosteroids, antisera, antibodies FK-506, tacrolimus, mycophenolatemofetil and primarily cyclosporines such as cyclosporine A.

The danger in using immunosuppressive agents lies in weakening the body's defence against infectious diseases and the increased risk of malignant diseases. Therefore, it is the object of the invention to provide a pharmaceutical preparation to be employed in transplantation medicine which may be used to treat, especially to suppress, weaken and/or alleviate host-versus-graft reactions but does not have the above disadvantage.

The object of the invention is achieved by using certain fumaric acid monoalkyl esters as salts with mono- or bivalent cations or in the form of the free acid, either alone or in combination with a dialkyl fumarate for preparing pharmaceutical compositions to be used in transplantation medicine. The subject matter of the invention is characterised in detail in the claims. The compositions according to the invention do not contain free fumaric acid per se.

It is known that pharmaceutical preparations which, upon biological degradation after administration, enter into the citric acid cycle or are part thereof gain increasing therapeutic significance—especially when given in high dosages—since they can alleviate or heal diseases caused cryptogenetically.

Fumaric acid, for example, inhibits the growth of the Ehrlich ascites tumour in mice, reduces the toxic effects of mitomycin C and aflatoxin [K. Kuroda, M. Akao, Biochem. Pharmacol. 29, 2839–2844 (1980)/Gann. 72, 777–782 (1981)/Cancer Res. 36, 1900–1903, (1976)] and displays a anti-psoriatic and anti-microbial activity [C. N. Huhtsnen, J. Food Sci. 48, 1574 (1983)/M. N. Islam, U.S. Pat. No. 4,346,118 dated Aug. 24, 1982/C.A. 97, 161317b (1982)].

When administered parenterally, transdermally and especially perorally, high dosages of fumaric acids or its derivatives known so far such as dihydroxyl fumaric acid, fumaramide and fumaronitrile have such unacceptably severe side effects and high toxicity [P. Holland, R. G. White, Brit. Dermatol. 85, 259–263 (1971)/M. Hagedorn, K. W. Kalkoff, G. Kiefer, D. Baron. J. Hug, J. Petres, Arch. Derm. Res. 254, 67–73 (1975)] that, in most cases, such a therapy had to be abandoned in the past.

European Patent Application 0 188 749 already describes fumaric acid derivatives and pharmaceutical compositions containing the same for the treatment of psoriasis. Pharmaceutical compositions for the treatment of psoriasis containing a mixture of fumaric acid and other fumaric acid derivatives are known from DE-A-25 30 372. The content of free fumaric acid is obligatory for these medicaments.

DE-A-26 21 214 describes medicaments containing the fumaric acid monoethyl ester and its mineral salts as active ingredient for the treatment of psoriasis. The publication "Hautarzt (Dermatologist) (1987) 279–285" discusses the use of fumaric acid monoethyl ester salts. Pharmaceutical compositions containing a mixture of fumaric acid monoalkyl ester salts and a fumaric acid diester for the treatment of psoriasis, psoriatic arthritis, neurodermatitis and enteritis regionalis Crohn are known from EP 0 312 697 B1.

Surprisingly, it has now been found that fumaric acid-$C_1$–$C_5$-monoalkylester(s) in the form of a salt thereof with mono- or bivalent cations, preferably in the form of calcium, magnesium, zinc or iron salts or lithium, sodium or potassium salts, or in the form of free acid, either alone or in combination with a di-$C_1$–$C_5$-alkyl-fumarate are advantageous for preparing a pharmaceu-tical composition for use in transplantation medicine. Compositions containing such fumaric acid $C_{1-5}$-monoalkyl esters surprisingly permit a positive modulation of the immune system in host-versus-graft reactions.

The invention preferably uses pharmaceutical compositions containing one or more compounds from the group consisting of calcium, magnesium, zinc and iron salts or lithium, sodium or potassium salts of fumaric acid monoalkyl esters of the general formula

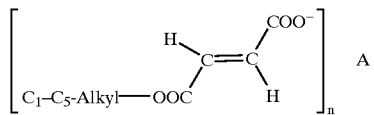

optionally in admixture with dialkyl fumarate of the formula

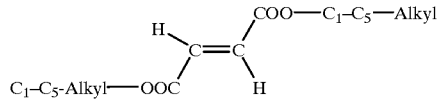

optionally together with customary pharmaceutical excipients and vehicles, wherein A is a bivalent cation from the series consisting of Ca, Mg, Zn or Fe or a monovalent cation from the series Li, Na or K, respectively, and n denotes the numeral 1 or 2 depending on the type of cation.

Pharmaceutical compositions containing one or more alkyl hydrogen fumarates of the general formula

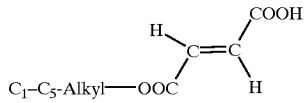

optionally in admixture with dialkyl fumarate of the formula

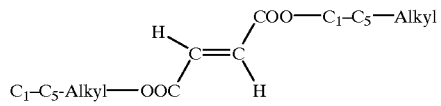

and, optionally, commonly used pharmaceutical excipients and vehicles, may also be used to advantage.

The use where the active ingredients are administered perorally in the form of tablets, micro-tablets, pellets or granulates in capsules or (soft or hard gelatine) capsules is preferred.

Preferred compositions according to the invention contain the calcium salt of the fumaric acid monomethyl ester or monoethyl ester or the calcium salt of the fumaric acid monomethyl ester or monoethyl ester in admixture with dimethyl fumarate.

Preparations containing the calcium salt of the fumaric acid monoalkyl ester or the fumaric acid alkyl ester in the form of the free acid in an amount of 10 to 300 mg are especially suitable for administration, the total weight of the active ingredients being 10 to 300 mg.

Other preferred oral forms of administration contain 10 to 290 parts by weight of the calcium salt of the fumaric acid monoalkyl ester and 290 to 10 parts by weight of dimethyl fumarate as well as 1 to 50 parts by weight of the zinc salt of the fumaric acid monoalkyl ester or 1 to 250 parts by weight of dimethyl fumarate, 1 to 50 parts by weight of the magnesium salt of the fumaric acid monoalkyl ester, for example monomethyl ester, the total weight of the active ingredients being 30 to 300 mg.

Preferred compositions according to the invention also contain the methyl hydrogen fumarate in an amount of 10 to 300 mg.

It is also possible to use the drugs in the form of compositions for percutaneous and transdermal administration and compositions for rectal administration.

The fumaric acid derivatives contained in the compositions according to the invention, are, for example obtained by
a) condensation of a compound of the formula

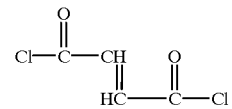

with 2 moles of dialkyl alcohol (ROH) by a known method to obtain a diester, followed by controlled hydrolysation to obtain a monoester, or
b) condensation with 1 mole of the relevant alkyl alcohol in the usual manner followed by hydrolysis of the monoacid chloride thus obtained to obtain an acid, or
c) direct condensation of the fumaric acid with 2 moles of alkyl alcohol (ROH) by a known method to obtain the relevant diester followed by controlled hydrolysation to obtain the monoester, or
d) direct condensation of maleic acid or maleic anhydride with 1–2 moles of the relevant alkyl alcohol (ROH) by a known method to obtain a mono- or diester followed by catalytic isomerisation to obtain the respective fumaric acid derivative.

The salts of the fumaric acid monoalkyl esters may also be obtained by reacting a compound of the general formula

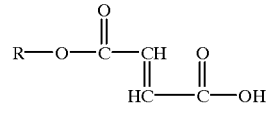

wherein R is a $C_1$–$C_5$ alkyl group with equivalent mole amounts of Na, K, Fe, Ca, Mg or Zn hydroxide or oxide in toluene and removing the water generated during the reaction.

For particularly preferred applications, compositions containing the following active ingredients in the stated dosages and proportions are used:
1) a pharmaceutical composition for peroral administration in the form of tablets, micro-tablets or pellets in capsules or capsules, characterised in that it contains the calcium salt of the fumaric acid monomethyl ester in an amount of 10 to 300 mg, the total weight of the active ingredients being 10 to 300 mg;
2) a pharmaceutical composition for peroral administration in the form of tablets, micro-tablets or pellets in capsules or capsules, characterised in that it contains 10 to 290 parts by weight of the calcium salt of the fumaric acid monomethyl ester and 290 to 10 parts by weight of dimethyl fumarate, the total weight of the active ingredients being 20 to 300 mg, 3) a pharmaceutical composition for peroral administration in the form of tablets, micro-tablets or pellets in capsules or capsules, characterised in that it contains 10 to 250 parts by weight of the calcium salt of the fumaric acid monomethyl ester, 1 to 50 parts by weight of dimethyl fumarate and 1 to 50 parts by weight of the zinc salt of the fumaric acid monomethyl ester, the total weight of the active ingredients being 20 to 300 mg, 4) a pharmaceutical composition for peroral administration in the form of tablets or capsules, characterised in that it contains 10 to 250 parts by weight of the calcium salt of the fumaric acid monomethyl ester, 250 to 10 parts of dimethyl fumarate, 1 to 50 parts by weight of the magnesium salt of the fumaric acid monomethyl ester and 1 to 50 parts by weight of the zinc salt of the fumaric acid monomethyl ester, the total weight of the active ingredients being 30 to 300 mg.

The following drug forms, dosages and proportions are also preferred:

5) a pharmaceutical composition for peroral administration, characterised in that it contains one or more compounds from the group of free acids of fumaric acid monoalkyl esters of the general formula

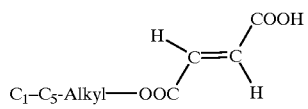

optionally in admixture with dialkyl fumarate of the formula

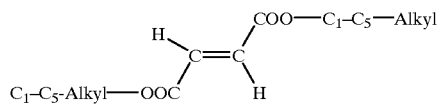

and vehicles, said compositions not containing fumaric acid in its free form;

6) a pharmaceutical composition for oral administration in the form of tablets, micro-tablets or pellets in capsules or capsules, characterised in that they contain alkyl hydrogen fumarate, preferably methyl hydrogen fumarate, in an amount of 10 to 30 mg, the total weight of the active ingredients being 10 to 300 mg.

7) a pharmaceutical composition for oral administration in the form of tablets, micro-tablets or pellets in capsules or capsules, characterised in that they contain 10 to 290 parts by weight of alkyl hydrogen fumarate, preferably methyl hydrogen fumarate, and 290 to 10 parts by weight of dialkyl fumarate, the total weight of the active ingredients being 20 to 300 mg.

Oral compositions may be covered by an enteric coating. Said compositions may be provided in the form of microtablets, pellets or granulates which may be contained in capsules. Such capsules may be soft or hard gelatine capsules.

According to a preferred embodiment, the size or the average diameter of the pellets or micro-tablets is in the range of 300 to 2000 μm, especially in the range of 500 or 1000 μm.

According to the invention the therapy with fumaric acid monoalkyl esters or salts thereof may also be carried out in combination with one or more compositions of the triple drug therapy commonly used in organ transplantations or with cyclosporine A, especially for the treatment, alleviation or suppression of host-versus-graft reactions.

For this purpose, the compositions administered may contain a combination of the active ingredients in known dosages or amounts. Likewise, a combination therapy may consist of the parallel administration of separate compositions by the same or a different route of application. Optionally, the dosage of the active ingredient contained in addition to the fumaric acid derivative dosage administered in accordance with the invention may be reduced with advantageous results.

Another embodiment of the use according to the invention is to alternate the drug therapy with immunosuppressive agents such as cyclosporine in sequence with an application of the above-mentioned fumaric acid derivatives. This means that an application of fumaric acid derivatives as defined above over one or more weeks may follow a cyclosporine therapy of one or more weeks. This permits reduction of the Cyclosporine A dosage resulting in a considerable decrease of the rate of side effects in long-term therapy.

In order to illustrate the use according to the invention, the following examples describe the composition of preferred drugs:

PRODUCTION EXAMPLES

Example 1

Preparation of Enteric-coated Film Tablets Containing 100.0 mg of Monoethyl Fumarate-Ca Aalt, which Corresponds to 71 mg of Fumaric Acid Taking the necessary precautions (breathing mask, gloves, protective clothing, etc.), 10.000 kg of monoethyl fumarate-Ca salt are crushed, mixed intensely and homogenised by means of an 800 sieve. Then an excipient mixture of the following composition is prepared: 21.000 kg of starch derivative (STA-RX 1500®), 2.000 kg of microcrystalline cellulose (Avicel PH 101®), 0.600 kg of polyvinyl pyrrolidone (PVP, Kollidon® 25), 4.000 kg of Primogel®, 0.300 kg of colloidal silicic acid (Aerosil®).

The active ingredient is added to the entire powder mixture, mixed, homogenised by means of a sieve 200 and processed with a 2% aqueous solution of polyvinyl pyrrolidone (PVP, Kollidon® 25) in the usual manner into binder granules, and then mixed with the outer phase in a dry state. The latter consists of 2.000 kg of a so-called FST complex containing 80% of talcum, 10% of silicic acid and 10% of magnesium stearate.

Thereafter the mixture is pressed into convex tablets with a weight of 400 mg and a diameter of 10.0 mm by the usual method. Instead of these classic compaction methods, other methods such as direct compaction or solid dispersions according to the melting and spray drying method may also be used for preparing tablets.

Enteric coating

A solution of 2.250 kg of hydroxy propyl methyl cellulose phthalate (HPMCP, Pharmacoat HP® 50) is dissolved in a solvent mixture consisting of 2.50 litres of demineralised water, 13.00 litres of acetone (Ph. Helv. VII) and 13.00 litres of ethanol (94% by weight) and then 0.240 kg of castor oil (Ph. Eur. II) added to the solution. The solution is poured or sprayed in portions onto the tablet cores in a coating pan in a conventional manner or applied by means of a fluidised-bed apparatus of the appropriate structure.

After drying, the film coating is applied. Said coating consists of a solution of Eudragit E 12.5% ® 4.800 kg, talcum (Ph. Eur. II) 0.340 kg, titanium(VI) oxide Cronus RN 56® 0.520 kg, coloured lacquer ZLT-2 blue (Siegle) 0.210 kg, and polyethylene glycol 6000 (Ph. Helv. VII) 0.120 kg in a solvent mixture of 8.200 kg of 2-propanol (Ph. Helv. VII), 0.060 kg of glycerine triacetate (Triacetin®) and 0.200 kg of demineralised water. After homogenous distribution in the coating pan or the fluidised bed, the mixture is dried and polished in the usual manner.

Example 2

Preparation of Enteric Coated Capsules Containing 86.5 mg of Monoethyl Fumarate-Ca Salt and 110.0 mg of Dimethyl Fumarate, which Corresponds to a Total of 150 mg of Fumaric Acid Taking the necessary precautions (breathing mask, gloves, protective clothing, etc.), 8.650 kg of monoethyl fumarate-Ca salt and 11.000 kg of dimethyl fumarate are intensely mixed with a mixture consisting of 15.000 kg of starch, 6.000 kg of lactose (Ph. Helv. VII), 2.000 kg of micro-crystalline cellulose (Avicel®), 1.000 kg of polyvinyl pyrrolidone (Kollidon® 25) and 4.000 kg of Primogel® and homogenised by means of a sieve 800.

Together with a 2% aqueous solution of polyvinyl pyrrolidone (Kollidon® 25) the entire powder mixture is processed in the usual manner into a binder granulate and mixed with the outer phase in the dried state. Said outer phase consists of 0.350 kg of colloidal silicic acid (Aerosil®), 0.500 kg of Mg stearate and 1.500 kg of talcum (Ph. Helv. VII). The homogeneous mixture is then filled in portions of 500.0 mg into appropriate capsules which are then provided with a enteric-coated (gastric-acid resistant) coating consisting of hydroxy propyl methyl cellulose stearate and castor oil as softening agent by a known method. Instead of hard gelatine capsules, the mixture may also be filled into appropriate gastric acid-resistant capsules, which consist of a mixture of cellulose acetate phthalate (CAP) and hydroxy propyl ethyl cellulose phthalate (HPMCP).

Example 3

Preparation of Enteric-coated Capsules Containing 203.0 mg of Monoethyl Fumarate-Ca Salt, 5.0 mg of Monoethyl Fumarate-Mg Salt and 3.0 mg of Monoethyl Fumarate-Zn Salt, which Corresponds to a Total of 150 mg of Fumaric Acid Taking the necessary precautions (breathing mask, gloves, protective clothing, etc.), 20.300 kg of mono ethyl fumarate-Ca salt, 0.500 kg of monoethyl fumarate-Mg salt and 0.300 kg of monoethyl fumarate-Zn salt are crushed, mixed intensely and homogenised using an sieve 800. A homogenous powder mixture of the following composition is mixed into this active ingredient mixture: spray-dried lactose 12.900 kg, colloidal silicic acid 1.000 kg, micro-crystalline cellulose (Avicel®) 2.000 kg, magnesium stearate (Ph. Helv. VII) 1.000 kg and talcum (Ph. Helv. VII) 2.000 kg. The entire powder mixture is homogenised once again by means of a sieve 2 filled into hard gelatine capsules with a net weight of 400 mg and sealed. The application of a gastric acidresistant coating is carried out in accordance with example 2.

Example 4

Preparation of Enteric-coated Micro-tablets in Capsules Containing 87.0 mg of Monoethyl Fumarate-Ca Salt, 120.0 mg of Dimethyl Fumarate, 5.0 mg of Monoethyl Fumarate-Mg Salt and 3.0 mg of Monoethyl Fumarate-Zn Salt, which Corresponds to a Total of 164 mg of Fumaric Acid ("Forte" Tablets)

Taking the necessary precautions (breathing mask, gloves, protective clothing, etc.), 8.700 kg of monoethyl fumarate-Ca salt, 12.000 kg of dimethyl fumarate, 0.500 kg of monoethyl fumarate-Mg salt and 0.30 kg of monoethyl fumarate-Zn salt are crushed, intensely mixed and homogenised by means of an sieve 800. Then an excipient mixture of the following composition is prepared: 18.00 kg of starch derivative (STA-RX 1500), 0.30 kg of micro-crystalline cellulose (Avicel PH 101), 0.75 kg of PVP (Kollidon 120), 4.00 kg of Primogel, 0.25 kg of colloidal silicic acid (Aerosil). The entire powder mixture is added to the active ingredient mixture, homogenised by means of a 200 sieve, processed in the usual manner with a 2% aqueous solution of polyvinyl pyrrolidone (Kollidon K25) to obtain a binder granulate and mixed in a dry state with the outer phase consisting of 0.50 kg of Mg stearate and 1.50 kg of talcum. Then the powder mixture is pressed by the conventional method into convex micro-tablets with a gross mass of 10.0 mg and a diameter of 2.0 mm. Instead of this classic tabletting method other methods for making tablets such as direct tabletting or solid dispersions by the melt method and the spray drying method may also be used.

The gastric acid-resistant coating may be poured or sprayed on in a classic coating pan or applied in a fluidised-bed apparatus. In order to achieve resistance to gastric acid, portions of a solution of 2.250 kg of hydroxy propyl methyl cellulose phthalate (HPMCP, Pharmacoat HP 50) are dissolved in a mixture of the following solvents: acetone 13.00 l, ethanol 94% by weight denatured with 2% ketone 13.50 l and demineralised water 2.50 l. 0.240 kg of castor oil are added as softening agent to the finished solution and applied in portions to the tablet cores in the usual manner.

Film-coat: After drying is completed, a suspension of the following composition is applied as a film-coat in the same apparatus: talcum 0.340 kg, titanium(VI) oxide Cronus RN 56 0.400 kg, coloured lacquer L red lacquer 86837 0.324 kg, Eudragit E 12.5% 4.800 kg and polyethylene glycol 6000 pH 11 XI 0.120 kg in a solvent mixture of the following composition: 2-propanol 8.170 kg, aqua demineralisata 0.200 kg and glycerine triacetate (Triacetin) 0.600 kg.

The gastric acid-resistant micro-tablets are then filled into hard gelatine capsules at a net weight of 500.0 mg and sealed.

Example 5

Preparation of Enteric-coated Film Tablets Containing 67.0 mg of Monoethyl Fumarate-Ca Salt, 30.0 mg of Dimethyl Fumarate, 5.0 mg of Monoethyl Fumarate-Mg Salt and 3.0 mg of Monoethyl Fumarate-Zn Salt, which Corresponds to 75 mg of Fumaric Acids ("Mite" Tablets)

Taking the necessary precautions (breathing mask, gloves, protective clothing, etc.), 3.000 kg of dimethyl fumarate, 6.700 kg of monoethyl fumarate-Ca salt, 0.500 kg of monoethyl fumarate-Mg salt and 0,300 kg of monoethyl fumarate-Zn salt are homogenised by means of an sieve 800.

An excipient mixture of the following composition is prepared in a similar manner to example 4, namely 30.000 kg of starch derivative (STA-RX 1500®), 3.000 kg of micro-crystalline cellulose (Avicel PH 101®), 0.750 kg of polyvinyl pyrrolidone (PVP, Kollidon® 25), 4.000 kg of Primogel, 0.250 kg of colloidal silicic acid (Aerosil®). The excipients and the mixture of active ingredients are mixed intimately and homogenised by means of a 200 sieve. With the aid of a 2% aqueous solution of polyvinyl pyrrolidone (PVP, Kollidon® 25), the mass is processed in the usual manner to obtain a binder granulate. A powder mixture of the following excipients is added to the dried granulate as an outer phase: 0.500 kg of Mg stearate (Ph. Eur.) and 0.800 kg of talcum (Ph. Eur. II).

The homogenous granulate mixture is pressed in the usual manner to obtain convex tablet cores having a weight of 500.0 mg and a diameter of 11.5 mm. In addition to binder methods other tabletting methods according to examples 1 and 4 may also be used. The application of a gastric acid-resistant coating and a filmcoat to the tablet cores is carried out as described analogously in examples 1 and 4.

The compositions according to the invention are preferably administered perorally in the form of tablets or capsules. These solid single-dosage medicaments are preferably provided with a gastric acid-resistant coating which, once having passed the stomach, is dissolved within a few minutes by the juice present in the small intestine and releases the active ingredient from the medicament. At the beginning and at the end of systemic treatment a lower dosage (mite) is required, whereas higher dosages (forte) are suitable for a regimen aft the initial phase.

Example 6

Preparation of Enteric-coated Film-tablets Containing 100.0 mg of Monomethyl Fumarate-Ca Salt, which Corresponds to 78 mg of Fumaric Acid Taking the necessary precautions (breathing mask, gloves, protective clothing, etc.), 10.000 kg of mono-methyl fumarate calcium salt are crushed, mixed and homogenised by means of an sieve 800. Then an excipient mixture with the following composition is prepared: 21.000 kg of starch derivative (STA-RX 1500®), 2.000 kg of micro-crystalline cellulose (Avicel PH 101), 0.600 kg of polyvinyl pyrrolidone (PVP, Kollidon® 25) 4.000 kg of Primogel, 0.300 kg of colloidal silicic acid (Aerosil®). The active ingredient is added to the mixture, mixed, homogenised by means of a sieve 200, processed in the usual manner with a 2% aqueous solution of polyvinyl pyrrolidone (Kollidon® K30) to obtain a binder granulate and then mixed in the dry state with the outer phase. Said outer phase consists of 2.000 kg of a so-called FST-complex containing 80% of talcum, 10% of silicic acid and 10% of magnesium stearate. Then the mixture is pressed in the usual manner to obtain convex tablets having a weight of 400 mg and a diameter of 10 mm. Instead of these classic tabletting methods other methods for preparing tablets such as direct tabletting and solid dispersions according to the melting and spray-drying method may also be used. The application of a gastric acid-resistant coating and a film-coat to the tablet cores is carried out analogously to examples 1 and 4.

Example 7

Preparation of Enteric-coated Film-tablets Containing 50.0 mg of Monomethyl Fumarate-Ca Salt, 50.0 mg of Dimethyl Fumarate, 5.0 mg of Monomethyl Fumarate-Mg Salt and 3.0 mg of Monomethyl Fumarate-Zn Salt, which Corresponds to 85 mg of Fumaric Acid Taking the necessary precautions (breathing mask, gloves, protective clothing, etc.), 5.000 kg of dimethyl fumarate, 5.000 kg of monomethyl fumarate-Ca salt, 0.500 kg of monomethyl fumarate-Mg salt and 0.300 kg of monomethyl fumarate-Zn salt are crushed, mixed and homogenised by means of an sieve 800. Then an excipient mixture with the following composition is prepared as described in example 4: 19.000 kg of starch derivative (STA-RX 1500®), 3.000 kg of micro-crystalline cellulose (Avicel PH 101®), 0.750 kg of polyvinyl pyrrolidone (PVP, Kollidon® 120) 4.000 kg of Primogel, 0.250 kg of colloidal silicic acid (Aerosil®).

The excipients and the active ingredient are mixed intensely, homogenised by means of a sieve 200, processed in the usual manner with a 2% aqueous solution of polyvinyl pyrrolidone (PVP, Kollidon® 25) to obtain a binder granulate and then mixed in the dry state with the outer phase. Said outer phase consists of 0.500 kg of magnesium stearate (Ph. Eur.) and 1.500 kg of talcum (Ph. Eur. II).

Then the entire granulate is pressed in the usual manner to obtain convex tablets having a weight of 400 mg and a diameter of 10 mm. Instead of these classic tabletting methods other methods for preparing tablets such as direct tabletting and solid dispersions according to the melting and spray-drying method may also be used.

The application of a gastric acid-resistant coating and a film-coat to the tablet cores is carried out analogously to examples 1 and 4.

Example 8

Preparation of Enteric-coated Film-tablets Containing 50.0 mg of Mono-n-propyl Fumarate-Ca Salt, which Corresponds to 32,8 mg of Fumaric Acid Taking the necessary precautions (breathing mask, gloves, protective clothing, etc.), 5.000 kg of mono-propyl fumarate-Ca salt are crushed, mixed and homogenised by means of a sieve 800. Then an excipient mixture with the following composition is prepared: 25.000 kg of starch derivative (STA-RX 1500®), 3.000 kg of micro-crystalline cellulose (Avicel PH 101®), 0.600 kg of polyvinyl pyrrolidone (PVP, Kollidon® 25), 4.000 kg of Primogel, 0.300 kg of colloidal silicic acid (Aerosil®). The active ingredient is added to the entire powder mixture, mixed, homogenised by means of a sieve 200, processed in the usual manner with a 2% aqueous solution of polyvidon pyrrolidone (Kollidon® K30) to obtain a binder granulate and then mixed in the dry state with the outer phase. Said outer phase consists of 2.000 kg of a so-called FST-complex containing 80% of talcum, 10% of silicic acid and 10% of magnesium stearate. Then the entire granulate is pressed in the usual manner to obtain convex tablets having a weight of 400 mg and a diameter of 10 mm. Instead of these classic tabletting methods other methods for preparing tablets such as direct tabletting and solid dispersions according to the melting and spray-drying method may also be used. The application of a gastric acid-resistant coating and a film-coat to the tablet cores is carried out analogously to examples 1 and 4.

Example 9

Preparation of Gastric-acid Resistant Pellets in Capsules Containing 50.0 mg of Monomethyl Fumarate-Ca Salt, 5.0 mg of Monomethyl Fumarate-Mg Salt and 3.0 mg of Monomethyl Fumarate-Zn Salt, which Corresponds to 45 mg of Fumaric Acid Taking the necessary precautions (breathing mask, gloves, protective clothing, etc.), 5.000 kg of mono-methyl fumarate-Ca salt, 0.500 kg of monomethyl fumarate-Mg salt and 0.300 kg of monomethyl fumarate-Zn salt are crushed, mixed intensely and homogenised by means of a sieve 400. At the same time, 2 l of a 20% (m/V) polyvinyl pyrrolidone (Kollidon K30) solution in ethanol is prepared. 7.250 kg of non-pareilles pellets are placed in a coating pan and sprayed with part of the Kollidon K30 solution until slightly moist. Then the active ingredient mixture is added in portions until the pellets are dry. This moistening/drying procedure is continued until all of the active ingredient mixture has been added. The remainder of the PVP solution is mixed with 0.720 kg of Eudragit E 12.5% solution and sprayed onto the pellets in its entirety. Finally, the pellets are moved around until completely dry. Instead of this method, other methods for preparing pellets may also be used, such as fluidised-bed coating or the extrusion-spherosination method. In addition, pellets containing the individual active ingredients may be prepared and then added in appropriate proportions after having been provided with a film-coat (see below).

The pellets are sprayed with Eudragit S 12.5% solution and dried with talcum. After each spraying/drying cycle the release of the active ingredient is measured and the addition of Eudragit S 12.5% solution/talcum continued until the release values meet the specification.

Then the enteric-coated pellets are filled into capsules (146 mg pellets/capsule).

Example 10

Preparation of Gastric-acid Resistant Capsules Containing 50.0 mg of Mono-iso-propyl Fumarate-Ca Salt, 50.0 mg of Di-iso-propyl Fumarate, 5.0 mg of Mono-iso-propyl Fumarate-Mg Salt and 3.0 mg of Mono-iso-propyl Fumarate-Zn Salt, which Corresponds to 67 mg of Fumaric Acid Taking the necessary precautions (breathing mask, gloves, protective clothing, etc.), 5.000 kg of mono-iso-propyl fumarate-Ca salt, 5.000 kg of di-iso-propyl fumarate, 0.500 kg of mono-iso-propyl fumarate-Mg salt and 0.300 kg of mono-iso-propyl fumarate-Zn salt are crushed, mixed intensely and homogenised by means of a sieve 800. Then a powder mixture with the following composition is mixed into this active ingredient mixture: 32.200 kg of spray-dried lactose, 2.000 kg of micro-crystalline cellulose (Avicel) and 1.000 kg of colloidal silicic acid (Aerosil®), 1.000 kg of magnesium stearate and 2.000 kg of talcum. The entire powder mixture is homogenised once more by means of a 200 sieve, filled into hard gelatine capsules at a net weight of 500 mg and sealed.

These capsules may then usually be provided with a enteric-coated coating consisting of hydroxy propyl methyl cellulose phthalate (HPMCP) and castor oil as softening agent. Instead of hard gelatine capsules, the active ingredient may also be filled into other gastric acid-resistant capsules which consist of a mixture of cellulose acetate phthalate (CAP) and hydroxy propyl ethyl cellulose acetate phthalate (HPMCP).

Example 11

Preparation of Micro-pellets in Capsules Containing 50.0 mg of Methyl Hydrogen Fumarate, which Corresponds to a Total of 44.6 mg of Fumaric Acid Taking the necessary precautions (breathing mask, gloves, protective clothing, etc.), 5.000 kg of methyl hydrogen fumarate are crushed and homogenised by means of a sieve 400. In addition, 2 l of a 20% (m/V) polyvinyl pyrrolidone (Kollidon K30) solution in ethanol are prepared. 7.250 kg of non-pareilles pellets are placed into a coating pan and sprayed with part of the Kollidon K30 solution until slightly moist. Then the active ingredient mixture is added in portions until the pellets are dry. This moistening/drying cycle is continued until all of the active ingredient mixture has been added. Finally, the pellets are moved around until they are completely dry. Instead of this method, it is also possible to use other methods for preparing pellets, such as fluidised-bed coating and the extrusion/spherosination method. In addition, the pellets may also be prepared with the individual active ingredients which are then added in the appropriate proportion after film-coating.

Then the pellets are filled in capsules (126.5 mg of pellets/capsule).

Examples of Application

The effect of calcium methyl fumarate for alleviating the host-versus-graft reaction both in acute and chronic rejection models was investigated on a rat kidney transplantation model.

Acute Rejection Model

In order to investigate the influence of calcium methyl fumarate on the acute rejection of the graft, animal experiments were carried out (on rats). For this purpose, two groups of rats were treated with calcium methyl fumarate (CaMF; dosage: 33.3 mg/kg/day) or a placebo for a total period of 56 days [28 days before the kidney transplantation (−28) to 28 days after transplantation (+28)]. The number of animals with results fit for evaluation were n=9 in the placebo group and n=12 in the verum group. After that, the survival time of the animals in days after the transplantation was evaluated. Table 1 shows the experimental results.

The significant increase in the average survival time in days after administration of calcium methyl fumarate clearly shows that this drug can suppress rejection, i.e. its influence on the host-versus-graft reaction is positive for transplantation medicine.

TABLE 1

| | Survival time of animals after kidney transplantation Days after transplantation | | | | | | | | | | | | |
|---|---|---|---|---|---|---|---|---|---|---|---|---|---|
| | 6 | 7 | 8 | 9 | 10 | 12 | 13 | 14 | 16 | 17 | 26 | 27 | >100 | Average survival time (in days) |
| | | | | | | Number of surviving animals | | | | | | | | |
| Placebo Group (Methocel) (Day −28–+28) | 9 | 9 | 8 | 2 | 2 | 2 | 2 | 2 | 2 | 2 | 2 | 2 | 2 | >28.3 ± 38.3 |

TABLE 1-continued

Survival time of animals after kidney transplantation
Days after transplantation

| | 6 | 7 | 8 | 9 | 10 | 12 | 13 | 14 | 16 | 17 | 26 | 27 | >100 | Average survival time (in days) |
|---|---|---|---|---|---|---|---|---|---|---|---|---|---|---|
| | | | | | | | Number of surviving animals | | | | | | | |
| Verum Group (CaMF) (Day −28—+28) | 12 | 12 | 12 | 11 | 10 | 9 | 8 | 7 | 6 | 5 | 5 | 4 | 4 | >42.3 ± 41.0 |

Chronic Rejection Model

In order to investigate the effect of calcium methyl fumarate on chronic rejection, three groups of rats received transplants (kidneys) in animal experiments. Groups 1 and 2 received a placebo (group 1) or calcium methyl fumarate (CaMF) (group 2) as active ingredient from day 28 before until day 28 after transplantation. The third group was given CaMF from day 30 to 60 after the kidney transplantation. All animals received cyclosporine from day 0 to 9 after the transplantation. The dosages administered were 1.5 mg/kg/day of cyclosporine (subcutaneously) and 33.3 mg/kg/day of CaMF (perorally).

The effect of the treatment was checked by measuring the creatinine levels in the serum, initially on day 0, 1, 3, 5, and 10 and then once a week, and by observing the urine protein levels which were measured once a week. In groups 1 and 2, n=10 animals each provided results suitable for evaluation; in group 3, n=9. The results of the treatment in week 10 after transplantation are shown in table 2.

After 10 weeks of follow-up so far, the animals treated with placebo showed a significant increase of the serum creatinine levels and increased proteinuria vis-a-vis the two verum groups, the pre-treated group 2 achieving even better results than group 3 which was treated later. These results indicate a significant inhibition of damage to the kidneys through calcium methyl fumarate.

TABLE 2

Chronic rejection model

| | Creatinine (μmoles/l) | Proteinuria (mg/24 hrs) |
|---|---|---|
| Group 1: Methocel (Day −28—+28) | 92,2 ± 60.8 | 76.1 ± 40.6 |
| Group 2: CaMF (Day −28—+28) | 55.7 ± 9.6 | 31.8 ± 18.4 |
| Group 3: CaMF (Day +30—+60) | 88.0 ± 42.4 | 52.5 ± 31.6 |

What is claimed is:

1. A method of treating host-versus-graft reactions, which method comprises administering to a patient in need thereof (a) one or more fumaric acid-$C_1$-$C_5$ monoalkyl ester(s) in the form of one or more salt(s) with mono- or bivalent cations, and/or (b) one or more fumaric acid-$C_1$-$C_5$ monoalkyl ester(s) in the form of free monocarboxylic acid(s), wherein optionally (a) and/or (b) is in combination with (c) a di-$C_1$-$C_5$ alkylfumarate.

2. A method according to claim 1 wherein:

(a) is represented by the formula

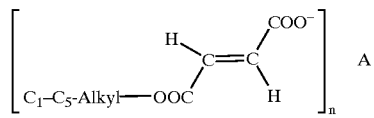

in which A is a bivalent Ca, Mg, Zn, or Fe cation or a monovalent Li, Na, or K cation, and n denotes the numeral 1 or 2 depending on the valence of the cation;

(b) is represented by the formula

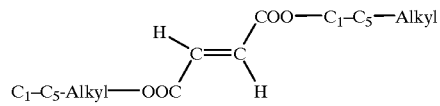

(c) is represented by the formula

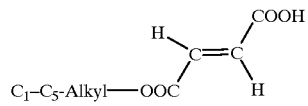

and wherein (a) and/or (b), and if present, (c), is/are optionally in combination with at least one pharmaceutically-acceptable excipient or carrier.

3. A method according to claim 1 wherein the calcium salt of fumaric acid monomethyl or monoethyl ester is administered.

4. A method according to claim 1 wherein one or more of the calcium, magnesium and/or zinc salts of fumaric acid monoethyl ester in admixture with dimethyl fumarate is/are administered.

5. A method according to any of claims 1, 2, 3, or 4 wherein (a) and/or (b) and optionally (c) are administered orally.

6. A method according to claim 5 wherein administration is in the form of tablets, microtablets, pellets, granules, or capsules.

7. A method according to claim 5 wherein administration is in the form of soft or hard gelatine capsules.

8. A method according to claim 5 wherein the total weight of (a) and/or (b), and if present, (c), per dosage is from 10 to 300 mg.

9. A method according to claim 1 wherein from 10 to 300 mg of the calcium salt of the fumaric acid monoalkyl ester, optionally, in combination with at least one pharmaceutically-acceptable excipient or carrier are administered.

10. A method according to claim 1 wherein a combination of (i) 10 to 290 parts by weight of the calcium salt of fumaric acid monoalkyl ester and (ii) 290 to 10 parts by weight of dimethyl fumarate, the total weight of (i) and (ii) being 20 to 300 mg, said combination optionally further including at least one pharmaceutically-acceptable excipient or carrier, is administered.

11. A method according to claim 1 wherein a combination of (i) 10 to 250 parts by weight of the calcium salt of fumaric acid monoalkyl ester, (ii) 1 to 50 parts by weight of dimethyl fumarate, and (iii) 1 to 50 parts by weight of the zinc salt of fumaric acid monoalkyl ester, the total weight of (i), (ii), and (iii) being 20 to 300 mg, said combination optionally further including at least one pharmaceutically-acceptable excipient or carrier, is administered.

12. A method according to claim 1 wherein a combination of (i) 10 to 250 parts by weight of the calcium salt of fumaric acid monoalkyl ester, (ii) 250 to 10 parts by weight of dimethyl fumarate, and (iii) 1 to 50 parts by weight of the magnesium salt of fumaric acid monoalkyl ester, the total weight of (i), (ii), and (iii) being 30 to 300 mg, said combination optionally further including at least one pharmaceutically-acceptable excipient or carrier, is administered.

13. A method according to claim 6 wherein the dosage forms are provided with an enteric coating.

14. A method according to any of claims 1, 2, 3, or 4 wherein a preparation for cutaneous and transdermal administration, or a preparation for parenteral administration, or a preparation for rectal administration is administered.

15. A method according to any of claims 1, 2, 3, 4, 9, 10, 11, or 12 wherein said method is carried out in combination with use of an immunosuppressive agent.

16. A method according to claim 15 wherein said immunosuppressive agent is cyclosporine applied in sequential or alternating manner with the application of the fumaric acid derivative(s).

17. A method according to claim 16 wherein (a) and/or (b), and if present, (c) is/are administered orally.

18. A method according to any of claims 1, 2, 3, 4, 9, 10, 11, or 12 wherein (a) and/or (b), and if present, (c) are administered in the form of pellets or micro-tablets having, respectively, a size or mean diameter in the range of 300 to 2000 $\mu$m.

* * * * *

UNITED STATES PATENT AND TRADEMARK OFFICE
CERTIFICATE OF CORRECTION

PATENT NO. : 6,359,003 B1
DATED : March 19, 2002
INVENTOR(S) : Joshi et al.

It is certified that error appears in the above-identified patent and that said Letters Patent is hereby corrected as shown below:

Title page,
Item [54], the title reads "USE OF FUMARIC ACID DERIVATIVES IN TRANSPLANT MEDICINE", and should read -- USE OF FUMARIC ACID DERIVATIVES IN TRANSPLANTATION MEDICINE --.

Column 1,
Line 5, reads "PCT/EP99/066110, fiked" and should read -- PCT/EP99/06110, filed --.
Line 6, reads "not English," and should read -- not in English --.

Signed and Sealed this

Twenty-fourth Day of September, 2002

Attest:

*Attesting Officer*

JAMES E. ROGAN
*Director of the United States Patent and Trademark Office*